United States Patent
Burgmair et al.

(10) Patent No.: US 7,719,004 B2
(45) Date of Patent: May 18, 2010

(54) SENSOR HAVING HYDROPHOBIC COATED ELEMENTS

(75) Inventors: Markus Burgmair, Regensburg (DE); Ignaz Eisele, Icking (DE); Thorsten Knittel, Pentling (DE)

(73) Assignee: Micronas GmbH, Freiburg (DE)

( * ) Notice: Subject to any disclaimer, the term of this patent is extended or adjusted under 35 U.S.C. 154(b) by 101 days.

(21) Appl. No.: 10/588,559

(22) PCT Filed: Feb. 1, 2005

(86) PCT No.: PCT/EP2005/050418

§ 371 (c)(1),
(2), (4) Date: May 31, 2007

(87) PCT Pub. No.: WO2005/075969

PCT Pub. Date: Aug. 18, 2005

(65) Prior Publication Data

US 2007/0262358 A1 Nov. 15, 2007

(30) Foreign Application Priority Data

Feb. 6, 2004 (DE) .................. 10 2004 005 927
Jul. 22, 2004 (DE) .................. 10 2004 035 551

(51) Int. Cl.
*H01L 23/58* (2006.01)
*H01L 33/00* (2010.01)
*G01N 7/00* (2006.01)
*G01N 9/00* (2006.01)
*G01N 19/10* (2006.01)
*G01N 25/00* (2006.01)
*G01N 29/02* (2006.01)
*G01N 27/00* (2006.01)
*G01N 31/00* (2006.01)
*G01N 33/00* (2006.01)
*G01N 35/00* (2006.01)
*G01N 37/00* (2006.01)
*G01P 15/00* (2006.01)
*G01P 21/00* (2006.01)

(52) U.S. Cl. .......... 257/48; 257/222; 257/226; 257/239; 257/252; 257/254; 257/414; 257/E23.001; 73/23.2; 73/488; 73/1.06; 73/1.37

(58) Field of Classification Search .............. 73/777, 73/23.2–31.07, 488–551, 700–756, 1.06, 73/1.37; 257/222, 226, 252–254, 48, 414–420, 257/239, E23.001, 213
See application file for complete search history.

(56) References Cited

U.S. PATENT DOCUMENTS 4,020,830 A * 5/1977 Johnson et al. ............. 600/348

(Continued)

FOREIGN PATENT DOCUMENTS

DE 103 35 163 3/2005 ............... 27/414

(Continued)

OTHER PUBLICATIONS

Gergintschew et al. "The capacitively controlled field effect transistor (CCFET) as a new low power gas sensor," Sensors and Actuators B, Elsevier Sequoia S.A., Lausanne, Ch., vol. 36, No. 1, Oct. 1996, pp. 285-289.

(Continued)

*Primary Examiner*—Phat X Cao
*Assistant Examiner*—Diana C Garrity
(74) *Attorney, Agent, or Firm*—O'Shea Getz P.C.

(57) ABSTRACT

The invention concerns a sensor with silicon-containing components from whose sensitive detection element electrical signals relevant to a present analyte can be read out by means of a silicon semiconductor system. The invention is characterized in that the silicon-containing components are covered with a layer made of hydrophobic material in order to prevent unwanted signals caused by moisture.

15 Claims, 3 Drawing Sheets

U.S. PATENT DOCUMENTS

| | | | |
|---|---|---|---|
| 4,269,682 A | 5/1981 | Yano et al. | 204/195 |
| 5,182,005 A | 1/1993 | Schwiegk et al. | 204/435 |
| 5,900,128 A | 5/1999 | Gumbrecht et al. | 204/415 |
| 2004/0067603 A1* | 4/2004 | Hagen | 438/106 |
| 2005/0103109 A1 | 5/2005 | Hegner et al. | 73/706 |
| 2007/0189931 A1* | 8/2007 | Ruhe et al. | 422/88 |

FOREIGN PATENT DOCUMENTS

| | | | |
|---|---|---|---|
| GB | 2 017 400 | 10/1979 | 27/26 |
| JP | 56100350 | 8/1981 | 27/30 |
| JP | 63171355 | 7/1988 | 27/30 |
| JP | 08189870 | 7/1996 | 9/12 |
| WO | WO 85/04480 | 10/1985 | |
| WO | WO 99/51975 | 10/1999 | 27/414 |

OTHER PUBLICATIONS

Angst et al., "Moisture Absorption Characteristics of Organosiloxane Self-Assembled Monolayers," Langmuir, American Chemical Society, New York, NY, US, vol. 7, No. 10, 1991, pp. 2236-2242, XP0023313481.

Wasserman et al., "Structure and Reactivity of Alkylsiloxane Monolayers Formed by Reaction of Alkyltrichlorosilanes on Silicon Substrates," Langmuir, American Chemical Society, New York, NY, US, vol. 5, No. 4, 1989, pp. 1074-1087, XP001006225.

Matsushima Toshinori et al., "Organic-inorganic field effect transistor with SnI-based perovskite channel layer using vapour phase deposition technique," Proceedings of the SPIE-The International Society for Optical Engineering, 2003, vol. 5217. pp. 43-54 (Abstract) CAPLUS [online].

Sudholter, Ernst et al., "Modification of ISFETs by covalent anchoring of poly(hydroxyetylmethacrylate)hydrogel. Introduction of thermodynamically defined semiconductor-sensing membrane interface." Analytica Chimica Acta, 1990, vol. 230, No. 1, pp. 59-65 (Abstract) CAPLUS [online].

* cited by examiner

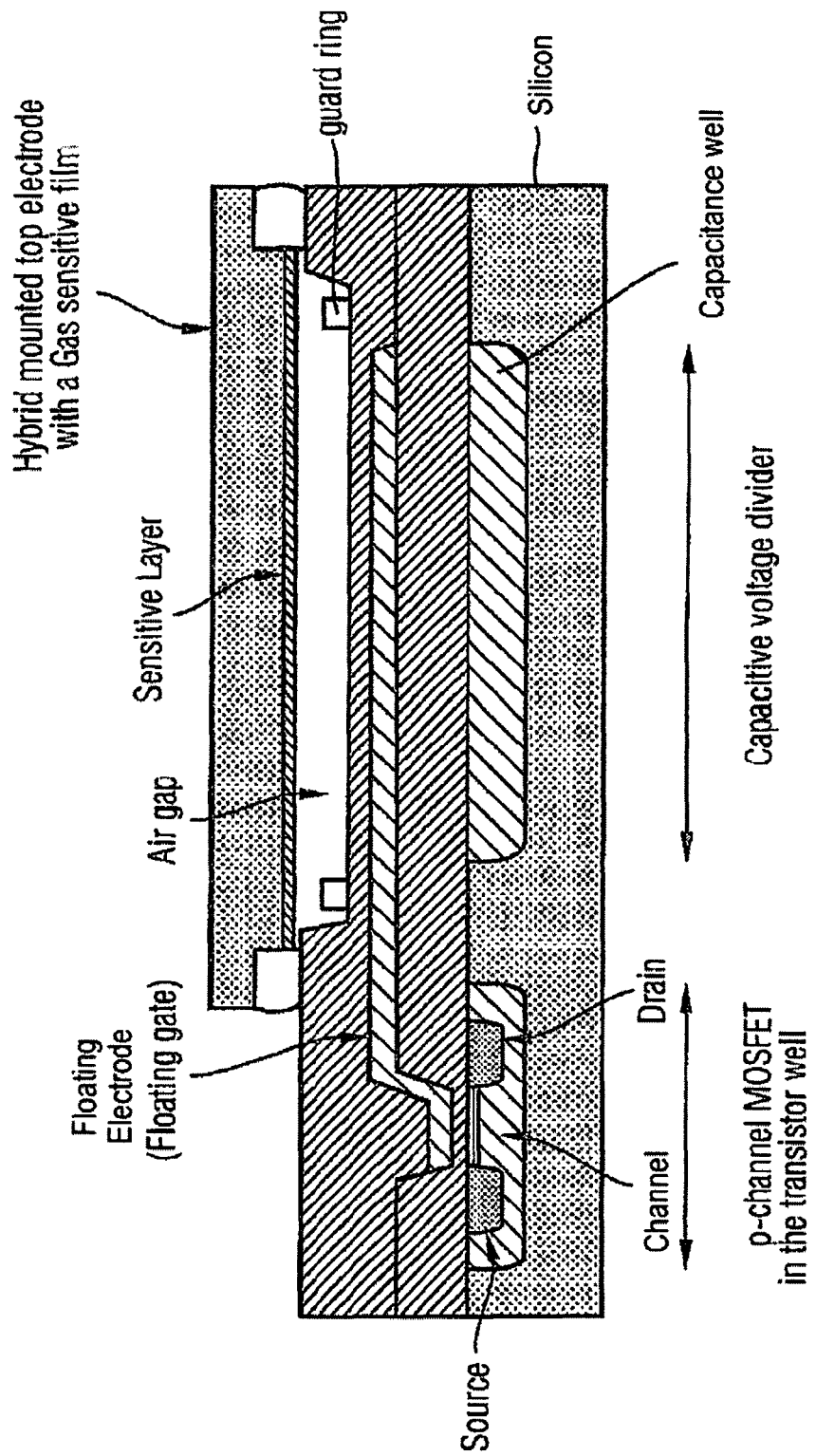

SENSOR HAVING HYDROPHOBIC COATED ELEMENTS

PRIORITY INFORMATION

This patent application claims priority from International patent application PCT/EP2005/050418 filed Feb. 1, 2005, German Patent Application No. 10 2004 005 927.6 filed Feb. 6, 2004, and German patent application 10 2004 035 551.7 filed Jul. 22, 2004, which are hereby incorporated by reference.

BACKGROUND OF THE INVENTION

This invention relates in general to sensors and in particular to a sensor, for example a gas sensor, acceleration sensor, or pressure sensor, with components containing silicon, where electrical signals can be read when analytes are present or in case of mechanical deformation. Moisture in the air forms a thin film of water on the surface of material containing silicon, which leads to increased surface conductivity. Leakage currents from this increased conductivity represent a problem with regard to stability and signal quality for many sensors that are in contact with air.

To prevent the effects of moisture on sensor systems, the sensors are encapsulated if possible. If contact with the surrounding air is necessary for proper operation of the sensor, for example gas sensors, passive water-repellent membranes may be used. Also, heating to temperatures well above 100° C. solves the problem, but this is associated with considerable expenditure of energy.

There is a need for a sensor with a semiconductor body whose moisture sensitivity and leakage current are substantially reduced.

SUMMARY OF THE INVENTION

Silanization familiar from glass coating can also be applied to semiconductor technology. In this case, a monolayer of the hydrophobic molecular chains that suppress the adsorption of water molecules is formed on a surface containing silicon. All hydrophobic molecular chains that participate in a stable bond with the surface are suitable for this application. Thus, no continuous water film that favors the unwanted surface conductivity can form, up to high atmospheric humidity levels—almost 100%.

Structural elements containing silicon can operate in ambient air after silanization without heating or encapsulation, and without the problem of interference from surface currents induced by moisture.

In general terms, the semiconductor body used as the base in this silicon technology is silanized. Either pure silicon or silicon compounds present superficially can be treated.

The fields of use of such semiconductor sensors based on silicon and insensitive to moisture, for example, are gas sensors, pressure sensors, or in general any sensors that come into contact with essentially atmospheric moisture when in operation. Hence analytes such as target gases are detected by gas sensors, and mechanical shape or deformation changes are detected by pressure sensors or acceleration sensors.

These and other objects, features and advantages of the present invention will become more apparent in light of the following detailed description of preferred embodiments thereof, as illustrated in the accompanying drawings.

BRIEF DESCRIPTION OF THE DRAWINGS

FIG. 3 is a cross-sectional illustration of a gas sensor in the form of a floating gate FET.

DETAILED DESCRIPTION OF THE INVENTION

Figure 1:
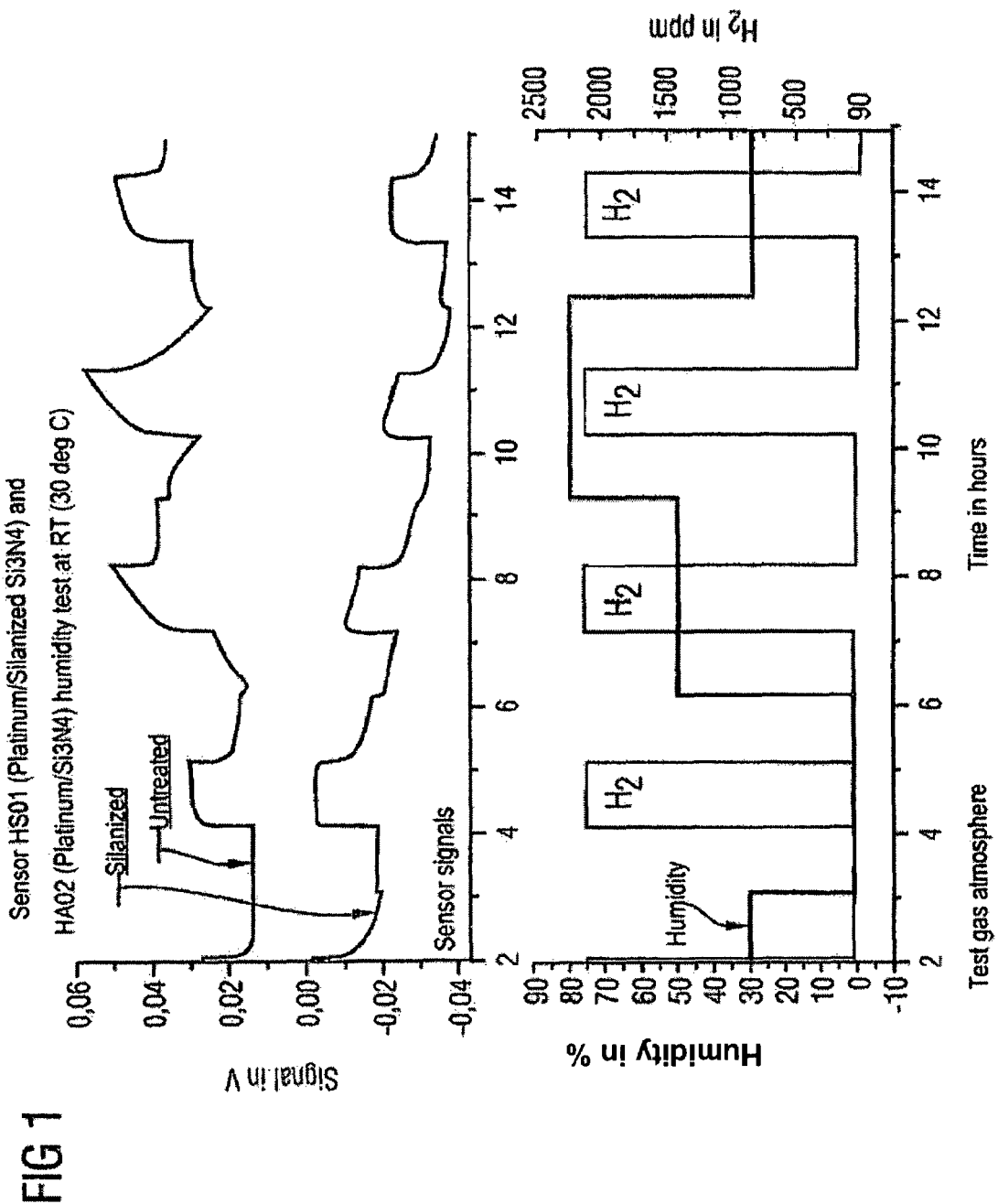
FIG. 1 is a graph that illustrates a comparison of a silanized hydrogen sensor and a sensor with no hydrophobic covering layer.

The functional principle of silanization on silicon nitride and oxidized polycrystalline silicon was tested specifically on a gas sensor, in particular a floating gate field effect transistor (FGFET). Other embodiments of FETs can also be used, for example suspended gate FETs. FIG. 3 illustrates schematically the structure of the FGFETs used. The potential change occurring on a sensitive layer from gas impingement is fed to the MOSFET by the voltage divider extending between a floating gate and a capacitive well (electrode), and leads to a current change between a drain and a source. A floating electrode (gate) is covered with a nitride or oxide layer to protect it against interfering leakage current. Nevertheless, potentials can still be coupled in capacitively through a conducting moisture film on this passivation. To prevent this, an equipotential surface, for example a guard ring, is placed on the surface around the sensitive gate. At higher atmospheric humidity levels (>50%), increased surface currents nevertheless occur, which lead to severe signal drift. To prevent this, it is necessary to prevent the formation of a moisture film. Hydrophobic molecular chains are then applied to the existing passivation by silanization before a hybrid gate is mounted. Since the adhesive bond of the gate then no longer adheres to this layer, additional aluminum-adhesive pads are necessary on the chip, since the silanization does not adhere there. Because of this process, the unheated gas sensors thus produced are almost completely stable even at high humidity levels. Subsequent measurement shows a comparison between a silanized hydrogen sensor and an untreated sensor at various humidity levels (see FIG. 1).

The sharp drift and "distortion" of the hydrogen signals is effectively suppressed by silanization. The remaining small moisture steps in the silanized signal are caused by the dipole signal of water on the sensitive platinum layer and no longer interfere.

Figure 2:
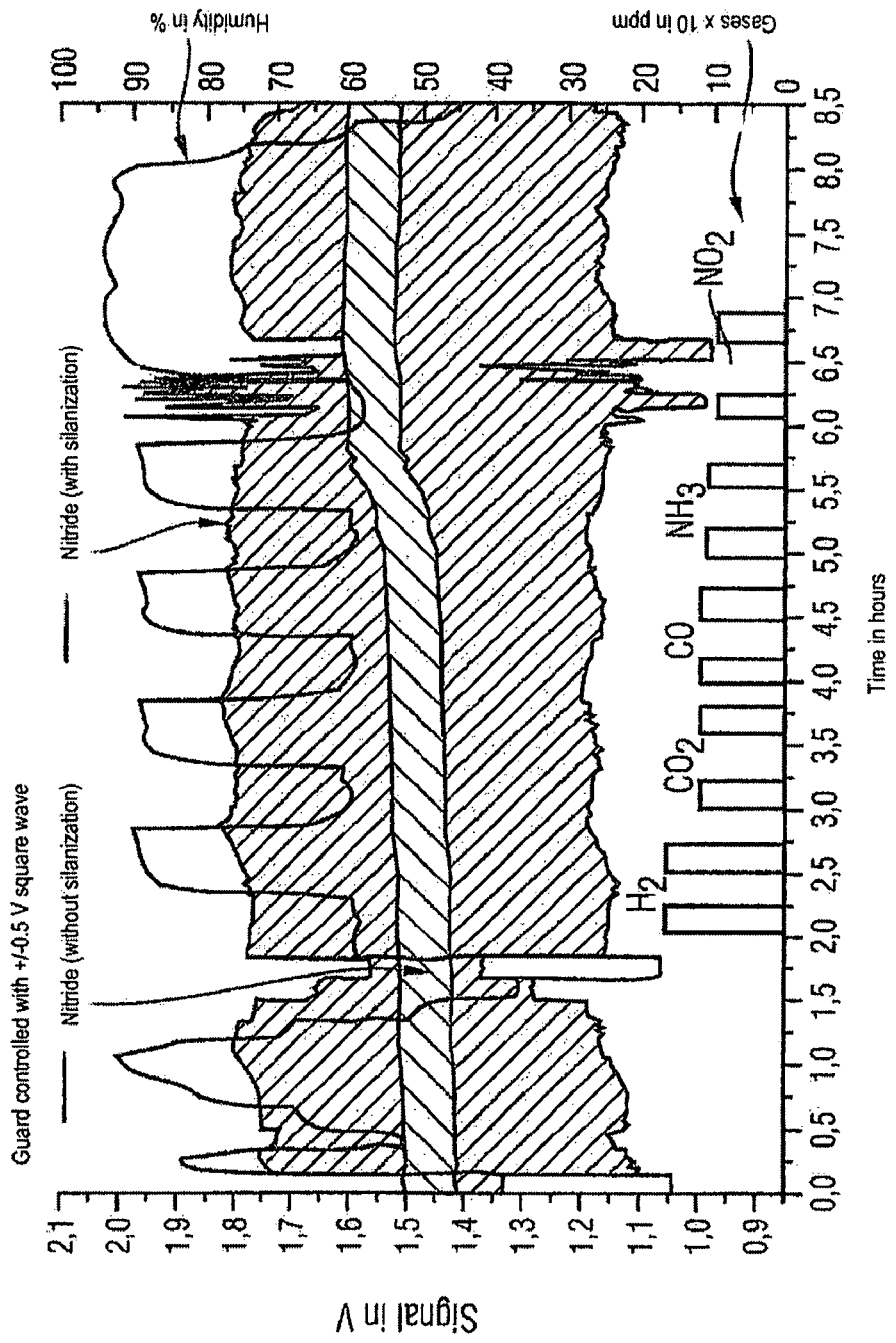
FIG. 2 is a graph that illustrates various humidity levels and additional gases.

To gain precise information on surface conductivity, the above FGFET was put together with surfaces with no hybrid gate, both silanized and unsilanized. To measure the very small currents qualitatively, use was made of the sensitivity of the floating gate. The guard ring was controlled in both chips with a square-wave generator and the moisture-dependent coupling to the transistors was measured. A very low frequency was chosen (0.1 Hz) to preclude frequency-dependent effects in the RC circuits. The higher the surface conductivity, the larger the coupling of the square-wave generator into the transistor. FIG. 2 illustrates a comparison of these measurements with various humidity levels and additional gases. The current in the transistors is kept constant by feedback electronics. The resulting signals originate from the feedback control circuit and thus show the potential applied to the floating gate.

It can be seen that all moisture effects have disappeared after silanization. The remaining coupling is only capacitive.

The reaction of the nitride to $NO_2$ has disappeared in the silanized version. Increased sensitivity to $NH_3$ exists instead. This is to be expected with the trichlorosilane used as the starting material for silanization, especially n-octadecyltrichlorosilane, since alkalis like ammonia attack the bonds to the nitride passivation. On the other hand, the layer is especially stable to acids (for example, $NO_2$). The samples with oxidized polysilicon show the same behavior.

Although the present invention has been illustrated and described with respect to several preferred embodiments thereof, various changes, omissions and additions to the form and detail thereof, may be made therein, without departing from the spirit and scope of the invention.

What is claimed is:

1. A sensor, comprising:
   a silicon substrate having a source region, a drain region and a capacitive well;
   a floating gate disposed on the silicon substrate to form a field effect transistor with the source region and drain region;
   an insulating layer that separates the floating gate and a hybrid mounted top electrode having a sensitive layer formed on an underside thereof, where the sensitive layer and the insulating layer form an air gap; and
   a layer of hydrophobic material on a surface of the insulating layer within the air gap.

2. The sensor of claim 1, where the hydrophobic layer comprises molecular chains that form a stable bond to silicon.

3. The sensor of claim 2, where the molecular chains form a monolayer.

4. The sensor of claim 1, where the silicon semiconductor system comprises a field effect transistor.

5. The sensor of claim 1, where the sensor comprises a sensor from the group including a gas sensor, a pressure sensor, and an acceleration sensor.

6. The sensor of claim 1, where the sensor comprises a gas sensor.

7. The sensor of claim 1, where the sensor comprises a pressure sensor.

8. The sensor of claim 1, where the sensor comprises an acceleration sensor.

9. The sensor of claim 1, where the hydrophobic coating layer is applied by silanization.

10. The sensor of claim 9, where a silane is used for the silanization.

11. The sensor of claim 9, where a trichlorosilane is used for the silanization.

12. The sensor of claim 9, where an n-octadecyltrichlorosilane ($C_{18}H_{37}Cl_3Si$) is used for the silanization.

13. A gas sensor, comprising:
    a silicon substrate having a source region, a drain region and a capacitive well;
    a floating gate disposed on the silicon substrate to form a field effect transistor with the source region and drain region;
    an insulating layer that separates the floating gate and a hybrid mounted top electrode having a gas sensitive layer formed on an underside thereof, where the gas sensitive layer and the insulating layer form an air gap; and
    a layer of hydrophobic material between the insulating layer and the air gap.

14. The sensor of claim 13, where the hydrophobic coating layer comprises molecular chains that form a stable bond to silicon.

15. The sensor of claim 14, where the molecular chains form a monolayer.

* * * * *